(12) United States Patent
Yang (10) Patent No.: US 10,391,025 B2
(45) Date of Patent: Aug. 27, 2019

(54) EYE MASSAGING DEVICE

(71) Applicant: Cheng-Chuan Yang, Taichung (TW)

(72) Inventor: Cheng-Chuan Yang, Taichung (TW)

(*) Notice: Subject to any disclaimer, the term of this patent is extended or adjusted under 35 U.S.C. 154(b) by 544 days.

(21) Appl. No.: 15/164,839

(22) Filed: May 25, 2016

(65) Prior Publication Data

US 2017/0340478 A1    Nov. 30, 2017

(30) Foreign Application Priority Data

May 18, 2016  (TW) .............................. 105207281 U (51) Int. Cl.
*A61H 23/02*    (2006.01)
*A61F 7/00*    (2006.01)
*A61F 7/02*    (2006.01)

(52) U.S. Cl.
CPC .............. *A61H 23/02* (2013.01); *A61F 7/007* (2013.01); *A61F 7/02* (2013.01); *A61F 2007/0004* (2013.01); *A61F 2007/0054* (2013.01); *A61F 2007/0072* (2013.01); *A61F 2007/0096* (2013.01); *A61F 2007/0228* (2013.01); *A61H 2201/0207* (2013.01); *A61H 2201/0242* (2013.01); *A61H 2201/165* (2013.01); *A61H 2201/5082* (2013.01); *A61H 2205/024* (2013.01)

(58) Field of Classification Search
CPC ............ A61H 23/02; A61H 2201/5082; A61H 2201/0207; A61H 23/0254; A61H 23/0263; A61H 2201/0221; A61H 2201/0242; A61H 2205/024; A61F 7/007; A61F 7/02; A61F 2007/0228; A61F 2007/0096; A61F 2007/0072; A61F 2007/0054; A61F 2007/0004
See application file for complete search history.

(56) References Cited

U.S. PATENT DOCUMENTS

| | | | | |
|---|---|---|---|---|
| 6,155,995 A | * | 12/2000 | Lin | ............................ A61F 7/02 601/148 |
| 2004/0059400 A1 | * | 3/2004 | Lin | ........................ A61F 7/007 607/109 |
| 2006/0200052 A1 | * | 9/2006 | Lin | .......................... A61H 5/00 601/70 |
| 2011/0251532 A1 | * | 10/2011 | Yang | .................. A61H 23/0263 601/18 |
| 2013/0281893 A1 | * | 10/2013 | Yang | .................. A61H 23/0263 601/15 |
| 2014/0277303 A1 | * | 9/2014 | Biser | ......................... A61F 7/02 607/104 |
| 2017/0181924 A1 | * | 6/2017 | Thorpe | .................. A61H 23/00 |

* cited by examiner

*Primary Examiner* — Quang D Thanh
(74) *Attorney, Agent, or Firm* — Rosenberg, Klein & Lee (57) ABSTRACT

An eye massaging device includes a main body, a water bag, a control unit, a cover, and a fixing ring. The temperature of the circulating water tank may be sensed by a thermal sensor and then feedback the temperature signal to a microprocessor. The microprocessor may control to drive a heating member to increase temperature and stop increasing temperature so as to effectively control the operation temperature and prevent from transient blindness resulting from being not able to effectively control the temperature.

5 Claims, 8 Drawing Sheets

EYE MASSAGING DEVICE

BACKGROUND OF THE INVENTION

1. Field of the Invention

The present invention relates to a massaging device, more particular relates to an eye massaging device for hot compressing on the eyes and controlling the temperature.

2. Description of Related Art

The eyes are used frequently, such as watching the monitor, TV, or tablet so that the eyes may become tired and unwell. In order to ease the fatigue and uncomfortability of the eyes, besides the eyes must rest appropriately, the muscles and acupoints around the eyes may be massaged to ease the eyes. Therefore, many eye massaging devices are developed.

The eye massaging device may be an airbag massager (such as Taiwanese patent no. M338070 and M288185) or a vibration massager for acupoints (such as Taiwanese patent no. M468311 and I314451). The convex particles of the airbag massager or the vibration massager may be activated by the motor to massage the eyes. However, the vibration is not useful and it is not effectively to activate blood circulation of the eyes.

The above mentioned massagers have many drawbacks, but the applicant had developed an eye massaging device which may hot and ice compress the eyes, such as Taiwanese patent no. M386892 and M503221. Since the energy (heat) is transmitted between the hot/cold hip and conduction member and between the liquid and the conduction member, the liquid is circulated in the water bag to adjust the temperature. The water bag with temperature may be compressed on the eyes to ease the eyes.

However, the above mentioned eye massaging device still have some drawbacks which are described as follows.

Firstly, although it may activate the blood circulation, the temperature may be not controlled precisely. Especially the human beings always depends on eyes to see and watch, the eye massage is more important. Therefore, the control of the liquid temperature while using the eye massaging device is the key point for development.

Secondly, the eyes are not flat but convex. The water bag of the eye massaging device is always directly contacted with the skin of the eyes. Although the upper eyelids may isolate the water bag to prevent from directly contacting with the eyes and the eye massaging device is not directly adjust the temperature to the eyes (in fact, the tissues around the eyes are hot compressed), the lenses of the eyes may still feel uncomfortable. The transient blindness may occur after being used for a long time. Therefore, the structure of the water bag must be modified to improve the bad influences for hot compressing eyes.

Thirdly, the liquid temperature may be not effectively controlled only by the hot/cold chip. It may be not make the temperature around the eyes uniform so as to influence the effects.

In view of the foregoing circumstances, the inventor has invested a lot of time to study the relevant knowledge, compare the pros and cons, research and develop related products. After quite many experiments and tests, the "eye massaging device" of this invention is eventually launched to improve the foregoing shortcomings, to meet the public use.

SUMMARY OF THE INVENTION

In order to improve above mentioned drawbacks, an eye massaging device may comprise a main body, having a front mounting portion and a rear mounting portion arranged opposite to each other, a circulating water tank, a heating member, and a circulating pump are arranged on the front mounting portion, the heating member is stacked on the circulating tank, and the heating member is fluidly communicated with the circulating water tank via a heating pipe; a water bag, arranged at the rear mounting portion, the water bag includes an outer frame portion, an affixing portion for touching a peripheral of two eyes, and a receiving portion, the affixing portion is arranged at an inner edge of the outer frame portion, and an peripheral of the receiving portion is arranged at the affixing portion, a flow guiding passage is formed between the receiving portion and the affixing portion, two concave areas are arranged at the affixing portion so as to avoid the eyes, a thickness of the affixing portion is thicker than a thickness of the outer frame portion, a circulating pipe is passed through the main body and then fluidly communicated with a location of the flow guiding passage between the circulating pump and the water bag and a location of the flow guiding passage between the circulating water tank and the water bag; a control unit, arranged at the front mounting portion of the main body, the control unit includes a thermal sensor for sensing a temperature of the circulating water tank and a microprocessor, the microprocessor is electrically connected to the thermal sensor, the circulating pump, and the heating member; a cover, used for receiving the circulating water tank, the heating member, the circulating pump, the control unit, the heating pipe, and part of the circulating pipe and fastened at the front mounting portion of the main body; and a fixing ring, surrounded a peripheral of the water bag and fixed at the rear mounting portion of the main body with the water bag.

The temperature of the circulating water tank may be sensed by the thermal sensor and then feedback the temperature signal to the microprocessor. The microprocessor may control to drive the heating member to increase temperature and stop increasing temperature so as to effectively control the operation temperature and prevent from transient blindness resulting from being not able to effectively control the temperature. In addition, when the affixing portion of the water bag is affixed on the eyes, the two concave areas may avoid (receive) the eyes to prevent from directly contacting with the eyes or being too close the eyes so as to reduce the bad influences resulting from directly hot patching the eyes.

The eye massaging device may further comprise two vibration motors which is electrically connected to the microprocessor, the two vibration motors are spaced apart from each other and arranged at the front mounting portion of the main body, and the two vibration motors are received by the cover.

In some embodiments, a heat dissipation space is defined between the receiving portion of the water bag and the rear mounting portion of the main body.

In some embodiments, the cover has a plurality of heat dissipation holes.

The eye massaging device may further comprise a belt, two ends of the belt are respectively buckled at two opposite sides of the main body.

The various objects and advantages of the present invention will be more readily understood from the following detailed description when read in conjunction with the appended drawing.

DETAILED DESCRIPTION OF THE INVENTION

To describe clearly that the present invention achieves the foregoing object and function, the technical features and desired function are described with reference to a preferred embodiment and accompanying drawings.

Please reference to FIGS. 1 to 4, an eye massaging device of the present invention may comprise a main body 1, a water bag 2, a control unit 3, a cover 4, and a fixing ring 5.

The main body 1 may have a front mounting portion 11 and a rear mounting portion 12 which are arranged opposite to each other. A circulating water tank 111, a heating member 112, and a circulating pump 113 are arranged on the front mounting portion 11. The heating member 112 is stacked on the circulating tank 111. The circulating pump 113 is fluidly communicated with the circulating water tank 111 via a heating pipe 114.

The main body 1 is an arc shell. The front mounting portion 11 is located at an arc convex side of the main body 1. The rear mounting portion 12 is located an arc concave side of the main body 1. The circulating water tank 111 is made of thermal conductive material and a tortuous heating passage (not shown) is arranged thereinside. One side of the heating member 112 is adhered on a surface of the circulating water tank 111 and then the circulating water tank 111 is fixed to the heating member 112 by screws for integrating. The circulating pump 113 is spaced apart from one side of the circulating water tank 111. The circulating pump 113 sucks the heating liquid in the circulating water tank 111 through the heating pipe 114.

Figure 5:
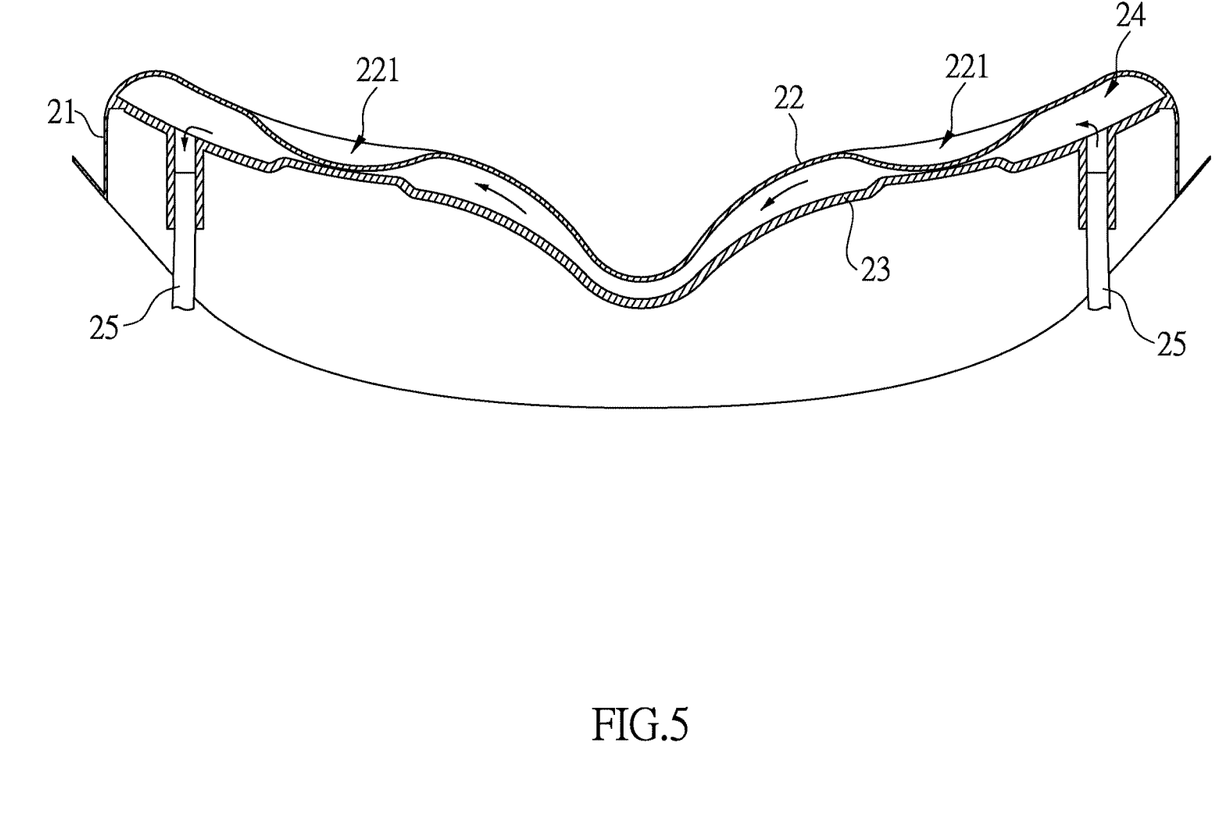
FIG. 5 is a cross-sectional view of the water bag of the eye massaging device of the present invention.
Figure 6:
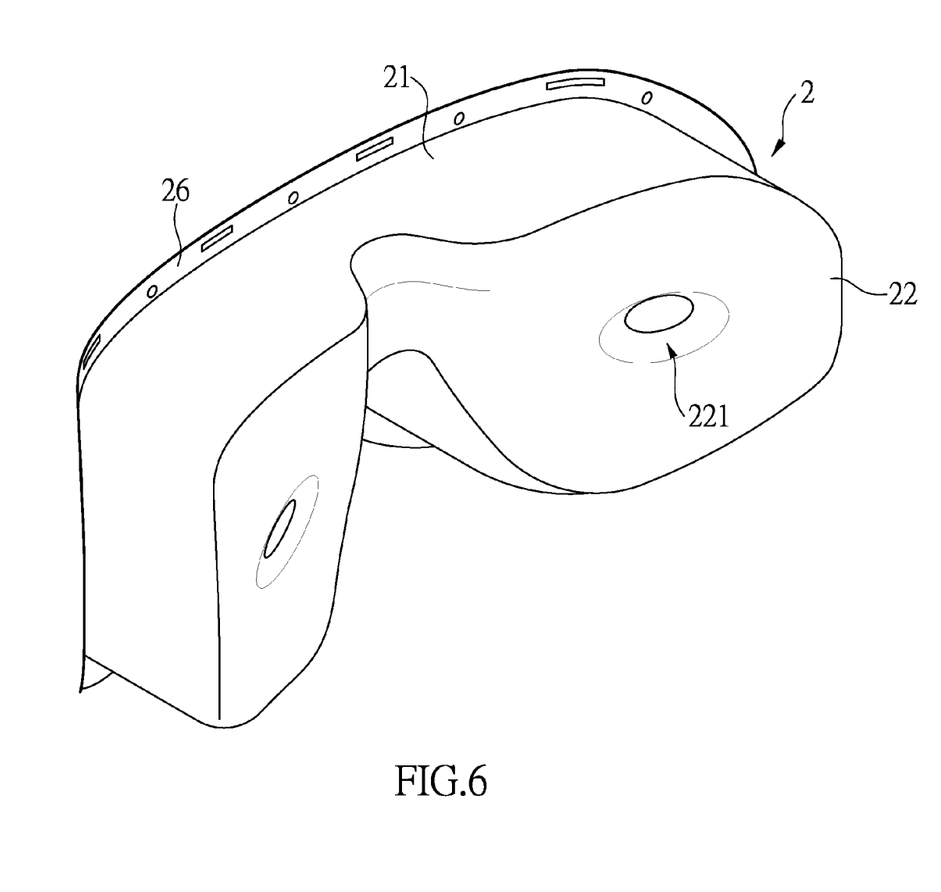
FIG. 6 is a perspective view of the water bag of the eye massaging device of the present invention viewed from another angle.

The water bag 2 may be arranged at the rear mounting portion 12 of the main body 1. Please refer to FIGS. 4 to 7, the water bag 2 may include an outer frame portion 21, an affixing portion 22 for touching a peripheral of two eyes, and a receiving portion 23. The affixing portion 22 is arranged at an inner edge of the outer frame portion 21. An peripheral of the receiving portion 23 is arranged at the affixing portion 22. In FIG. 5, a flow guiding passage 24 is formed between the receiving portion 23 and the affixing portion 22. Two concave areas 221 are arranged at the affixing portion 22 so as to avoid the eyes. A thickness of the affixing portion 22 is thicker than a thickness of the outer frame portion 21. A circulating pipe 25 is passed through the main body 1 and then fluidly communicated with a location of the flow guiding passage 24 between the circulating pump 113 and the water bag and a location of the flow guiding passage 24 between the circulating water tank 111 and the water bag 2. The water bag 2 is made of heat resistant and extensible material. The concave areas 221 are spherical concave shapes from the affixing portion 22 toward the receiving portion 23. An outer ring portion 26 is arranged at a peripheral of the outer frame portion 21. A heat dissipation 27 is defined among the receiving portion 23 of the water bag 2, the outer frame portion 21, and the rear mounting portion 12 of the main body 1.

The control unit 3 may be arranged at the front mounting portion 11 of the main body 1. The control unit 3 includes a thermal sensor 31 for sensing a temperature of the circulating water tank 11 and a microprocessor 32 (such as micro controlling unit, MCU). The microprocessor 32 is electrically connected to the thermal sensor 31, the circulating pump 113, and the heating member 112.

The heating member 112 is controlled by the microprocessor 32. The temperature may be increased or stopped after the heating member 112 is controlled and driven by the microprocessor 32. The temperature of the liquid in the circulating water tank 111 is sensed by the thermal sensor 31 and the temperature signal is transmitted to the microprocessor 32. The microprocessor 32 is judged if the current temperature is higher than a preset temperature. If the current temperature is higher than the preset temperature, the heating member 112 is stopped operating. If the current temperature is lower than the preset temperature, the heating member 112 is kept operating. The microprocessor 32 is controlled the circulating pump 113 to activate the circulation of the liquid and shut down the circulating pump 113 to stop circulating liquid. Please refer to FIGS. 2 and 3, the circulation means that the liquid is flowed through the circulating water tank 111, the circulating pump 113, and the water bag 2 in series, and then back to the circulating water tank 111.

The cover 4 is used for receiving the circulating water tank 111, the heating member 112, the circulating pump 113, the control unit 3, the heating pipe 114, and part of the circulating pipe 25 and fastened at the front mounting portion 11 of the main body 1. The cover 4 has a concave receiving groove 41 for receiving the circulating water tank 111, the heating member 112, the circulating pump 113, the control unit 3, the heating pipe 114, and part of the circulating pipe 25. The cover 4 has a plurality of heat dissipation holes 42 which are space apart from one another. The heat dissipation holes 42 are fluidly communicated with the concave receiving groove 41.

The fixing ring 5 is surrounded a peripheral of the water bag 2 and fixed at the rear mounting portion 12 of the main body 1 with the water bag 2. One side of the fixing ring 5 is pressed against the outer ring portion 26 of the water bag 2 and the water bag 2 is fastened at the rear mounting portion 12 so that the outer ring portion 26 of the water bag 2 is pressed and fastened by the rear mounting portion 12 of the main body 1 and the fixing ring 5 in two opposite directions.

The temperature of the eye massaging device of the present invention may be controlled at 40° C. which is set as the default temperature in general operation. The low-temperature patch is ranged from 38° C. to 40° C. and the high-temperature patch is ranged from 40° C. to 42° C. And 42° C. is set to be a critical temperature in high temperature. If the thermal sensor 31 is sensed a temperature higher than 42° C. (critical temperature), the microprocessor 32 may obtain the temperature signal and stop driving the heating member 112. If the thermal sensor 31 is sensed a temperature lower than 38° C., the microprocessor 32 may obtain the temperature signal and drive the heating member 112 to increase the temperature. Besides, if the microprocessor 32 may not obtain the temperature signal, the microprocessor 32 is judged to be in an abnormal status and stop the heating member 112 to increase the temperature so as to prevent from the thermal sensor 31 from being damaged or transmitting no temperature signal.

Figure 7:
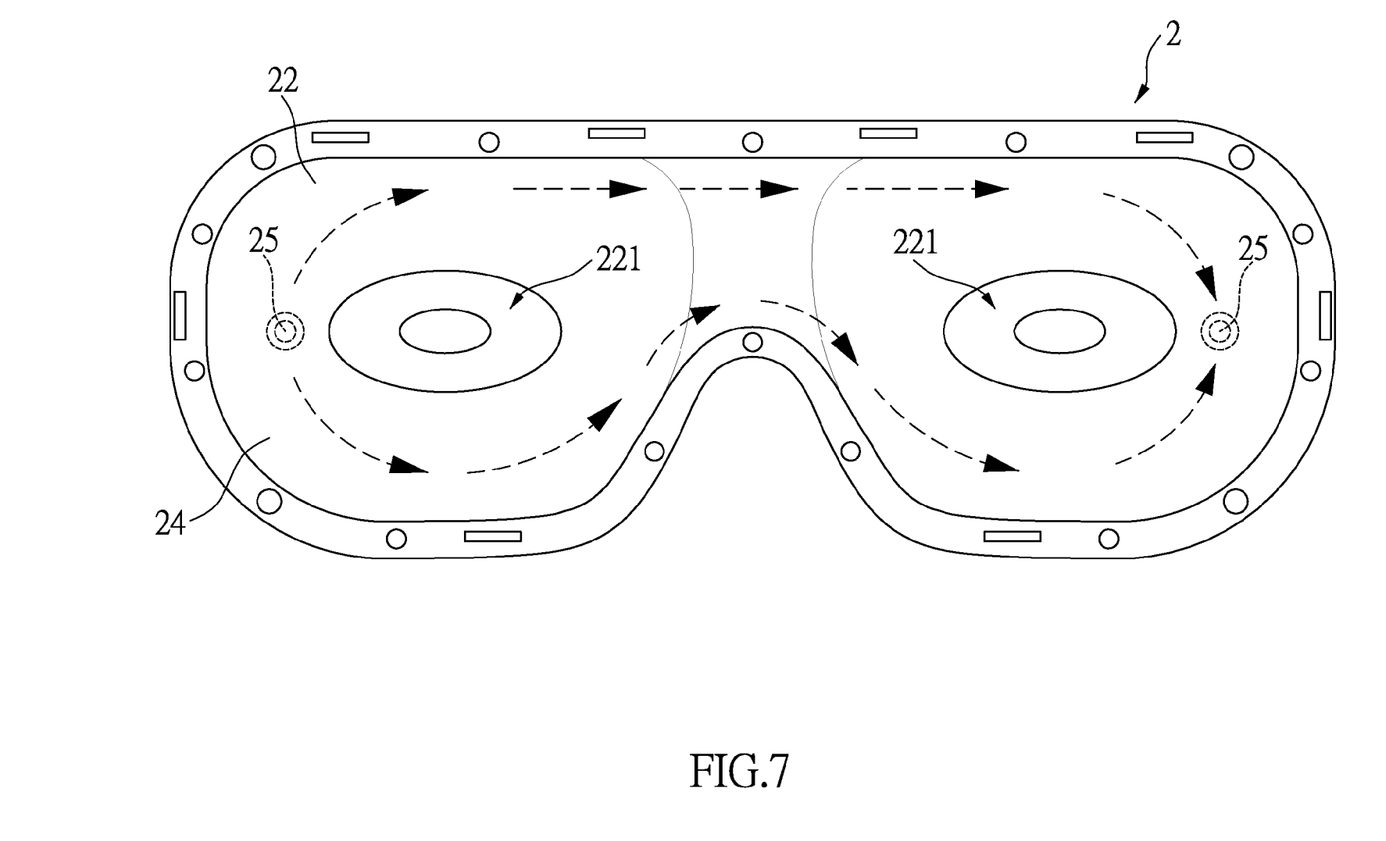
FIG. 7 is a view of the water bag of the eye massaging device of the present invention while guiding the flow.

The temperature of the circulating water tank 111 may be sensed by the thermal sensor 31 and then feedback the temperature signal to the microprocessor 32. The microprocessor 32 may control to drive the heating member 112 to increase temperature and stop increasing temperature so as to effectively control the operation temperature and prevent from transient blindness resulting from being not able to effectively control the temperature. In addition, when the affixing portion 22 of the water bag 2 is affixed on the eyes, the two concave areas 221 may avoid (receive) the eyes to prevent from directly contacting with the eyes or being too close the eyes so as to reduce the bad influences resulting from directly hot patching the eyes. In FIG. 7, the liquid is flowed through the peripherals of the two concave areas 221 and the flow path is like ∞ shape while the liquid is flowed in the flow guiding passage 24 of the water bag 2. According to above descriptions, the temperature of the circulating water tank 111 may be immediately sensed and the heating member 112 may be effectively controlled if increasing the temperature or stopping increasing the temperature so as to achieve the effect of temperature control since the microprocessor 32 is electrically connected to the thermal sensor 31 and the heating member 112.

Furthermore, in FIG. 5, the thickness of the affixing portion 22 is thicker than the thickness of the outer frame portion 21 so that the affixing portion 22 of the water bag 2 may isolate the heat from transmitting and prevent the eyes from being burned indirectly by the high-temperature liquid.

Figure 1:
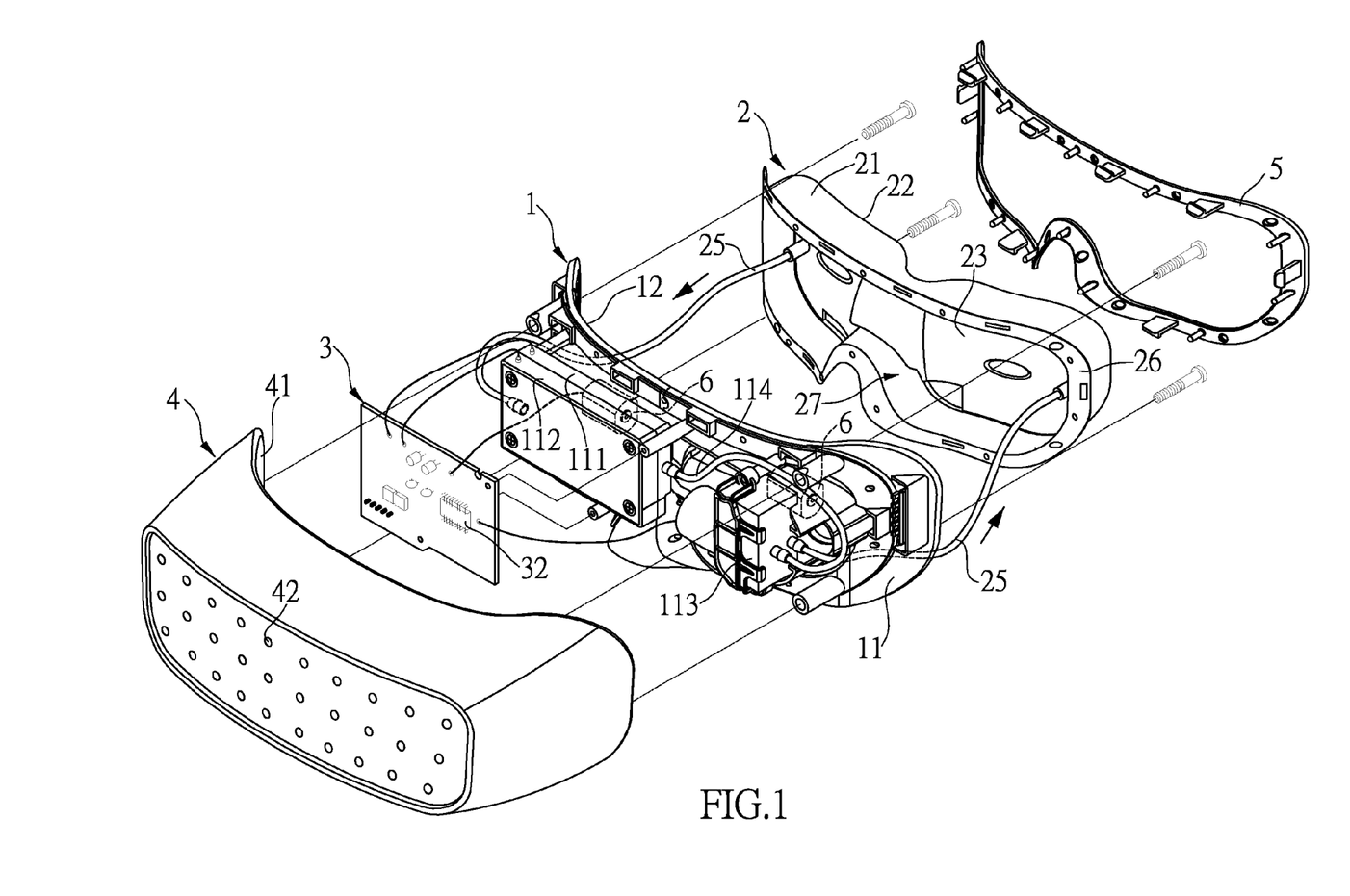
FIG. 1 is an exploded view of an eye massaging device of the present invention.
Figure 2:
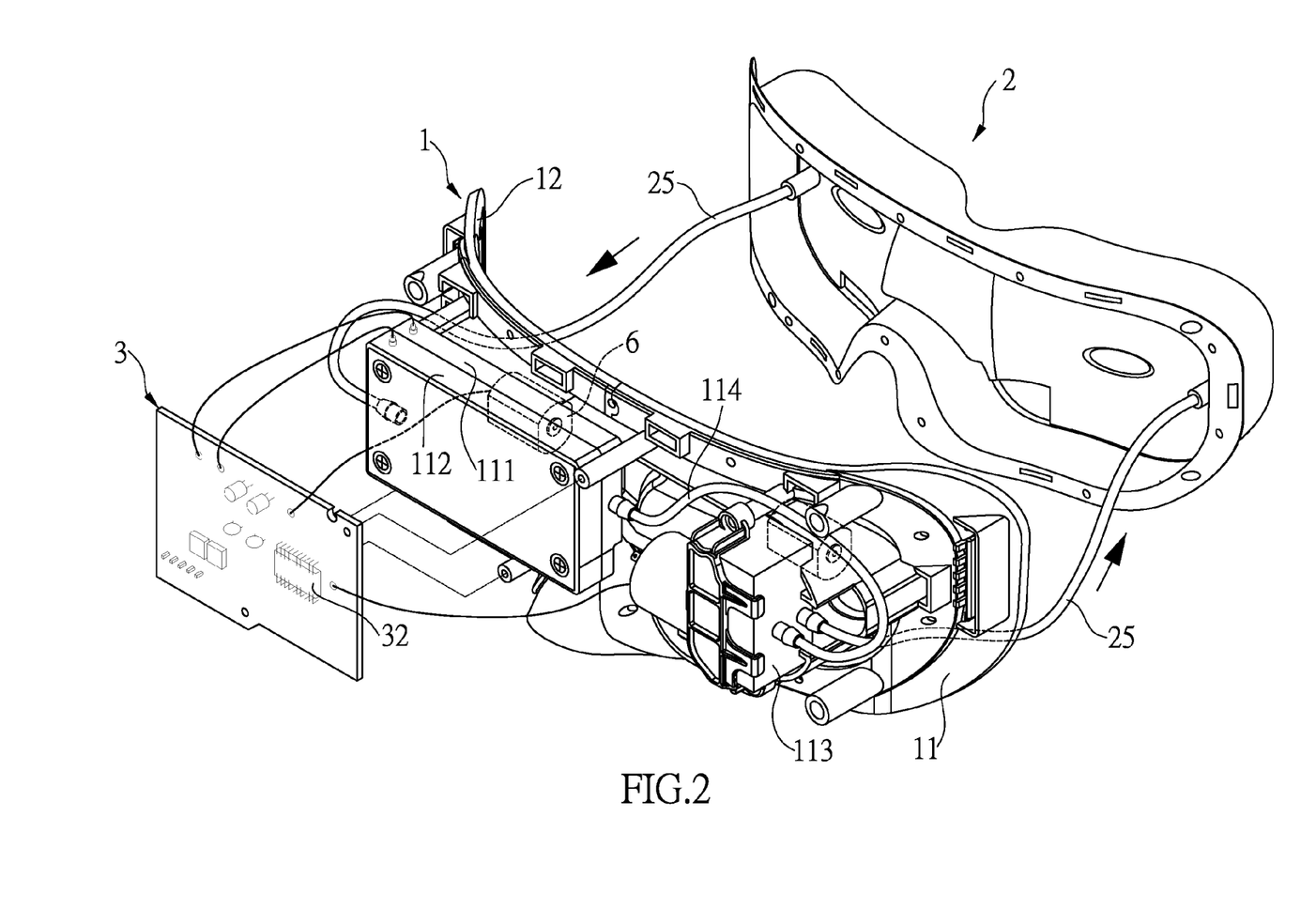
FIG. 2 is a partial exploded view of the eye massaging device of the present invention.
Figure 3:
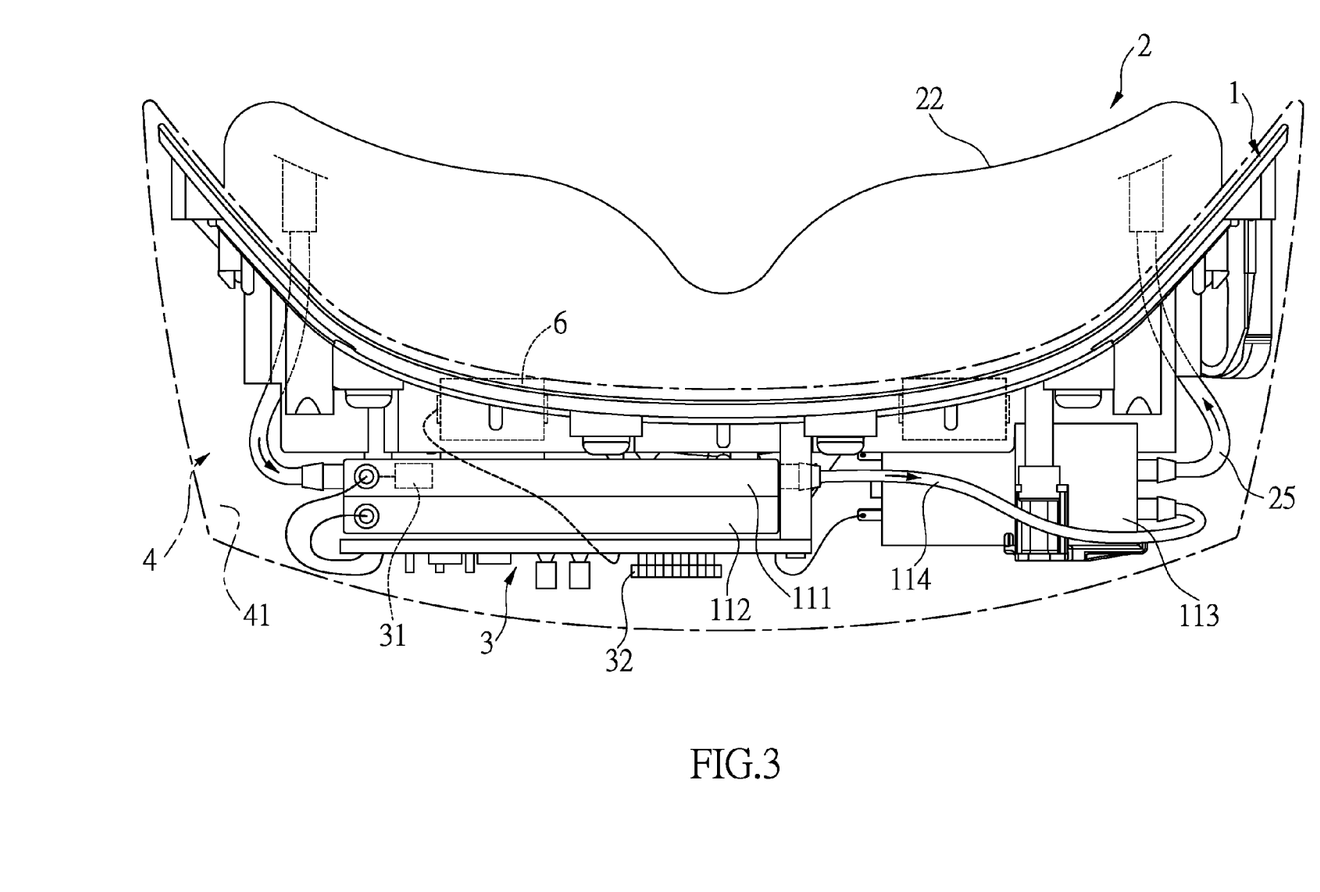
FIG. 3 is a perspective view of the eye massaging device of the present invention.
Figure 4:
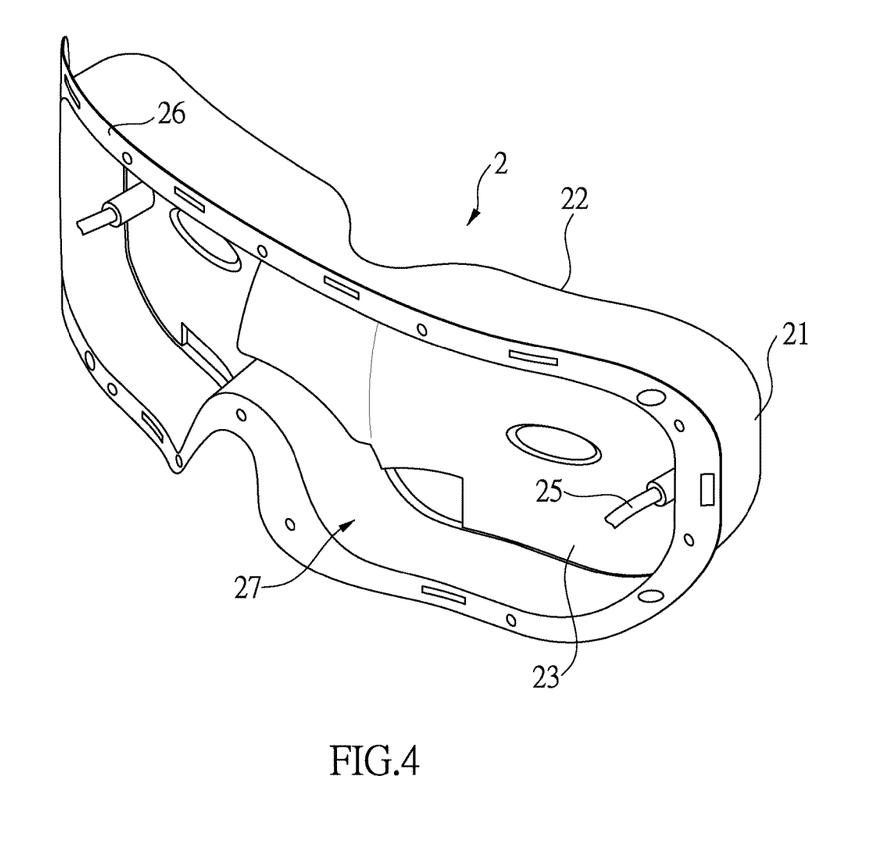
FIG. 4 is a perspective view of a water bag of the eye massaging device of the present invention.

Please refer to FIGS. 1 to 3, the eye massaging device of the present invention may further comprise two vibration motors 6. The two vibration motors 6 may be electrically connected to the microprocessor 32. The two vibration motors 6 are spaced apart from each other and arranged at the front mounting 11 of the main body 1. The two vibration motors 6 are received by the cover 4. Since the vibration motors 6 are arranged at the front mounting portion 11 of the main body 1 and the affixing portion 22 of the water bag 2 is directly contacted with the eyes, the microprocessor 32 may drive the vibration motors 6 to vibrate the water bag 2 indirectly and apply on the eyes.

Figure 8:
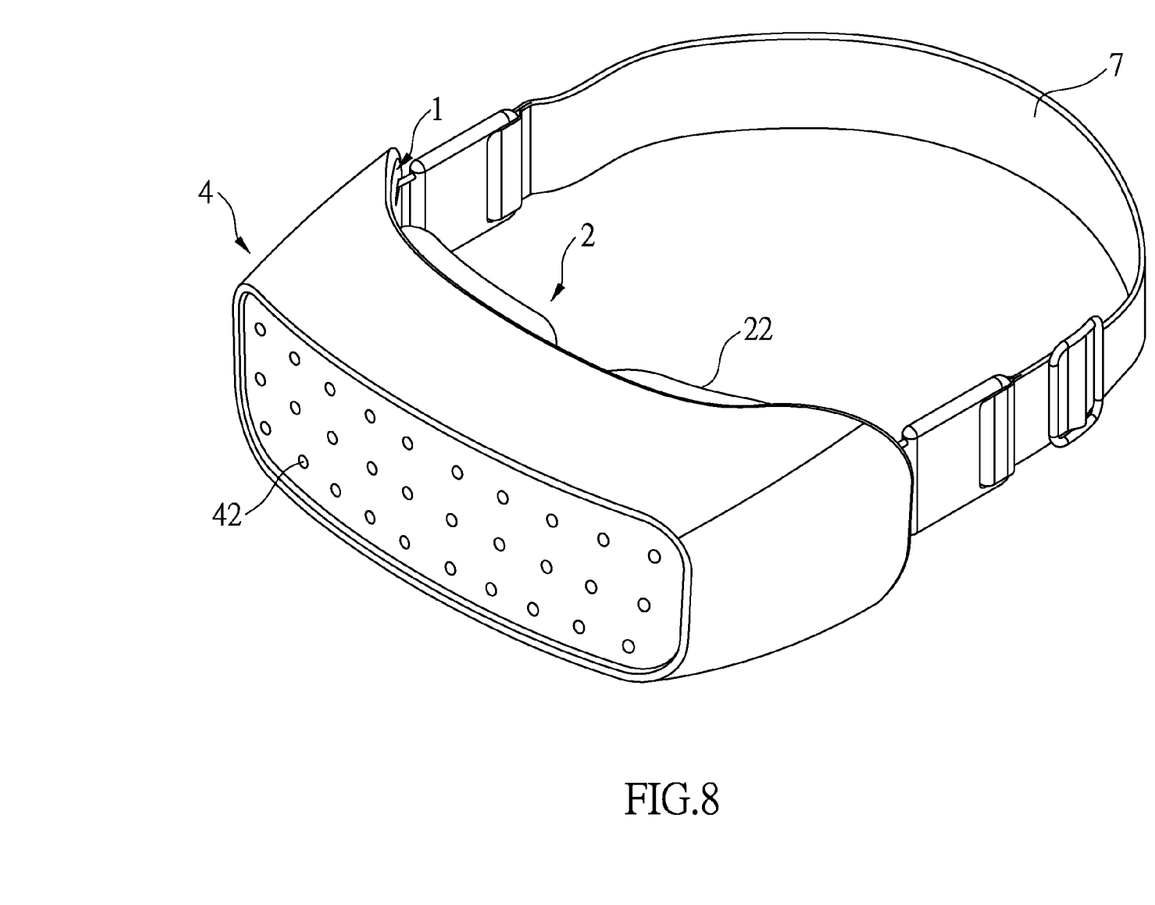
FIG. 8 is a perspective view of the eye massaging device of the present invention while being assembled with a belt.

In FIG. 8, the eye massaging device of the present invention may further comprise a belt 7. Two ends of the belt 7 are respectively buckled at two opposite sides of the main body 1. The belt 7 may be buckled the main body 1 on head of a user so as to make the affixing portion 22 of the water bag 2 firmly fasten and abut against the eyes.

The foregoing descriptions are merely the exemplified embodiments of the present invention, where the scope of the claim of the present invention is not intended to be limited by the embodiments. Any equivalent embodiments or modifications without departing from the spirit and scope of the present invention are therefore intended to be embraced.

The disclosed structure of the invention has not appeared in the prior art and features efficacy better than the prior structure which is construed to be a novel and creative invention, thereby filing the present application herein subject to the patent law.

What is claimed is:

1. An eye massaging device, comprising:
a main body, having a front mounting portion and a rear mounting portion arranged opposite to each other, a circulating water tank, a heating member, and a circulating pump are arranged on the front mounting portion, the heating member is stacked on the circulating water tank, and the circulating pump is fluidly communicated with the circulating water tank via a heating pipe;
a water bag, arranged at the rear mounting portion, the water bag includes an outer frame portion, an affixing portion for touching a peripheral of two eyes, and a receiving portion, the affixing portion is arranged at an inner edge of the outer frame portion, and an peripheral of the receiving portion is arranged at the affixing portion, a flow guiding passage is formed between the receiving portion and the affixing portion, two concave areas are arranged at the affixing portion so as to avoid the eyes, a thickness of the affixing portion is thicker than a thickness of the outer frame portion, a circulating pipe is passed through the main body, a first portion of the circulating pipe is fluidly communicated between the circulating pump and a location of the flow guiding passage of the water bag, and a second portion of the circulating pipe is fluidly communicated between the circulating water tank and another location of the flow guiding passage of the water bag;
a control unit, arranged at the front mounting portion of the main body, the control unit includes a thermal sensor for sensing a temperature of the circulating water tank and a microprocessor, the microprocessor is electrically connected to the thermal sensor, the circulating pump, and the heating member;
a cover, used for receiving the circulating water tank, the heating member, the circulating pump, the control unit, the heating pipe, and part of the circulating pipe and fastened at the front mounting portion of the main body; and
a fixing ring, surrounded a peripheral of the water bag and fixed at the rear mounting portion of the main body with the water bag.

2. The eye massaging device as claimed in claim 1, further comprising two vibration motors electrically connected to the microprocessor, the two vibration motors are spaced apart from each other and arranged at the front mounting portion of the main body, and the two vibration motors are received by the cover.

3. The eye massaging device as claimed in claim 1, wherein a heat dissipation space is defined between the receiving portion of the water bag and the rear mounting portion of the main body.

4. The eye massaging device as claimed in claim 3, wherein the cover has a plurality of heat dissipation holes.

5. The eye massaging device as claimed in claim 4, further comprising a belt, two ends of the belt are respectively buckled at two opposite sides of the main body.

* * * * *